United States Patent
Chang et al.

(10) Patent No.: US 11,668,702 B2
(45) Date of Patent: Jun. 6, 2023

(54) REGULATION OF FUNGAL FRUITING BODY DEVELOPMENT

(71) Applicant: The Chinese University of Hong Kong, Hong Kong (CN)

(72) Inventors: Jinhui Chang, Hong Kong (CN); Hoi Shan Kwan, Hong Kong (CN); Man Chun Wong, Hong Kong (CN); Po Lam Chan, Hong Kong (CN); Yichun Xie, Hong Kong (CN); Wing Chee Beatrice Ho, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 0 days.

(21) Appl. No.: 16/137,134

(22) Filed: Sep. 20, 2018

(65) Prior Publication Data
US 2019/0145958 A1 May 16, 2019

Related U.S. Application Data

(60) Provisional application No. 62/586,732, filed on Nov. 15, 2017.

(51) Int. Cl.
| | |
|---|---|
| *C12N 11/02* | (2006.01) |
| *G01N 33/50* | (2006.01) |
| *C12N 9/12* | (2006.01) |
| *C12N 15/80* | (2006.01) |

(52) U.S. Cl.
CPC .......... *G01N 33/5008* (2013.01); *C12N 9/12* (2013.01); *C12N 15/80* (2013.01); *C12N 2310/20* (2017.05); *C12Y 207/11026* (2013.01); *G01N 2333/91215* (2013.01); *G01N 2500/00* (2013.01); *G01N 2500/04* (2013.01)

(58) Field of Classification Search
None
See application file for complete search history.

(56) References Cited

U.S. PATENT DOCUMENTS 9,072,776 B2 * 7/2015 Kristiansen ........ A61K 39/0002

OTHER PUBLICATIONS

Seffernick et al. (J. Bacteriology, vol. 183, pp. 2405-2410, 2001).*
Wells (Biochemistry, vol. 29, pp. 8509-8517, 1990).*
Ma et al. (Glycoconj J., 2014, 31:355-363).*
Qin et al. (Scientific Reports, 2015, 5:8504, 1-8).*
De Assunção, et al. "Enrichment of mushrooms: an interesting strategy for the acquisition of lithium." Food chemistry 134, No. 2 (2012): 1123-1127.
Kirby, et al. "Glycogen synthase kinase 3 (GSK3) inhibitor, SB-216763, promotes pluripotency in mouse embryonic stem cells." PloS one 7, No. 6 (2012): e39329.
Mleczek, et al. "Cultivation of mushrooms for production of food biofortified with lithium." European Food Research and Technology 243, No. 6 (2017): 1097-1104.
Passmore, et al. "The eukaryotic translation initiation factors eIF1 and eIF1A induce an open conformation of the 40S ribosome." Molecular cell 26, No. 1 (2007): 41-50.
Westermarck, Jukka. "Regulation of transcription factor function by targeted protein degradation: an overview focusing on p53, c-Myc, and c-Jun." In Transcription Factors, pp. 31-36. Humana Press, Totowa, NJ, 2010.
Wildman, H. G. "Lithium chloride as a selective inhibitor of *Trichoderma* species on soil isolation plates." Mycological Research 95, No. 12 (1991): 1364-1368.
You, et al. "A quantitative model for mRNA translation in *Saccharomyces cerevisiae*." Yeast 27, No. 10 (2010): 785-800.
Cross, et ak. "Inhibition of glycogen synthase kinase-3 by insulin mediated by protein kinase B." Nature 378, No. 6559 (1995): 785.
Harwood, et al. "Glycogen synthase kinase 3 regulates cell fate in Dictyostelium." Cell 80, No. 1 (1995): 139-148.
He, Xi, Jean-Pierre Saint-Jeannet, James R. Woodgett, Harold E. Varmus, and Igor B. Dawid. "Glycogen synthase kinase-3 and dorsoventral patterning in Xenopus embryos." Nature 374, No. 6523 (1995): 617.
Li, et al., "Regulation and Function of Glycogen Synthase Kinase 3," J Med Mol Biol Dec. 31, 2006, No. 5, vol. 3, pp. 383-386.
Plyte, et al. "Glycogen synthase kinase-3 (GSK-3) is regulated during Dictyostelium development via the serpentine receptor cAR3." Development 126, No. 2 (1999): 325-333.
Teo, et al. "Glycogen synthase kinase-3 is required for efficient Dictyostelium chemotaxis." Molecular biology of the cell 21, No. 15 (2010): 2788-2796.

* cited by examiner

*Primary Examiner* — Hope A Robinson
(74) *Attorney, Agent, or Firm* — Kilpatrick Townsend & Stockton LLP

(57) ABSTRACT

The present invention provides for a fungus, especially in the form of fungal mycelium, that has altered glycogen synthase kinase-3 (GSK-3) expression and/or activity level and therefore exhibits modified characteristics in fruiting body development. Also provided are compositions and methods for generating living fungal mycelium with altered fruiting body development.

10 Claims, 12 Drawing Sheets

| Spreadings on broken sites | "Heat" group | "Lithium" group |
|---|---|---|
| YMG broth | The broken sites are apart | Bind with new hyphae |
| ddH$_2$O | The broken sites are apart | Loosely bind by new hyphae |

REGULATION OF FUNGAL FRUITING BODY DEVELOPMENT

RELATED APPLICATION

This application claims priority to U.S. Provisional Patent Application No. 62/586,732, of the same title, filed Nov. 15, 2017, the contents of which are hereby incorporated by reference in the entirety for all purposes.

BACKGROUND OF THE INVENTION

Fungi are important to carbon cycle of the ecosystem in that they degrade lignin and cellulose of plants. The life cycle of mushroom-forming fungi starts from the basidiospores geminating for mycelial growth. Upon environmental stimuli, including nutrient depletion, light/dark cycle, and cold shock, mycelia aggregate into hyphal knot, followed by fruiting body initials. Initials then develop into stage-1 and -2 primordia, young and mature fruiting bodies.

Mycelium is mainly composed of natural polymers, namely, chitin, polysaccharides, proteins, etc. Mycelium-based biomaterials have a wide range of applications due to their controlled and tunable properties during growth. The dried mycelium has strength, durability, and many other beneficial qualities: it is nontoxic, fire-resistant, mold resistant, water-resistant, and a great thermal insulator, amongst other salient features.

Under proper circumstances, mycelium of many basidiomycetous fungi will aggregate to form mushrooms, which are the fruiting body spreading the basidiospores. The fruiting bodies will cause conformational changes of the mycelium based materials, while the spores may cause allergy and infection in susceptible population. In current production procedures of the mycelium-based materials, all living mycelium cells are killed by heat or fungicide to preventing the fruiting body formation.

As the cells are rendered inert during the manufacturing process, these existing products of mycelium-based materials retain few of the benefits of the biological components they contain, for example, the ability to respond to environmental cues or to self-repair. The living system is also the foundation to leverage biological abilities of the mushroom to produce self-healing materials, and form environmentally responsive protective outer layers, for example, increased porosity, changed appearance or color, or varied tensile strength to achieve a functional response to a specific stimulus. Therefore, new approaches are needed for inhibiting fruiting body formation while keeping the mycelium alive, in order to produce living mycelium-based materials of desirable qualities.

This invention provides a biochemical approach to regulate fruiting body formation. This invention also enables one to apply this approach in producing living mycelium-based biomaterials, of which stability as well as self-healing ability are demonstrated. In this invention, *Coprinopsis cinerea* is used to represent the white-rot basidiomycetous fungi, as it is a classic model mushroom-forming fungus. The typical life cycle of *C. cinerea* can be finished within 2 weeks under lab condition, which includes stages of vegetative mycelium, hyphal knots, initial, stage-1 and -2 primordia, young and mature fruiting bodies.

Kinases, as one of the largest protein families, account for about 2% of eukaryotic genomes. Phosphorylation of proteins kinases affects their activity, localization, stability, conformation, and protein-protein interaction. Kinases mediate cellular and developmental responses to growth factors, environmental signals, and internal processes, and the kinases cascades play crucial roles in many signaling transduction pathways.

One interesting and putatively central regulatory kinase is glycogen synthase kinase-3 (GSK-3). GSK-3 is a serine/threonine kinase of the CMGC family of proline-directed kinases that is highly conserved in all eukaryotes. GSK-3 is activated by the constitutive phosphorylation at a C-terminal tyrosine residue, however, the regulatory phosphorylation at an N-terminal serine residue causes a conformational change to block the catalytic domain, hence inhibits its kinase activity (Takahashi-yanaga 2013). The kinases PKA, PKB, and PKC inhibit GSK-3 in specific signaling pathways in eukaryotes, while in fungi these kinases are essential growth regulators in response to environmental stimuli.

In mammals, GSK-3 inhibition has attracted widespread attention as one of the critical therapeutic targets whereby lithium exerts its pharmacological effects on mood stabilization, neurogenesis, neurotrophicity, neuroprotection, anti-inflammation, and others. Lithium is not absorbed through the skin during spa use (PubChem Compound Database). Lithium compounds are also suggested to be added in cultivation to fortify the lithium nutrient value of some edible mushrooms (Mleczek et al. 2017; De Assunão et al. 2012). Lithium chloride (LiCl) is a well-known substance that has been shown to inhibit GSK-3 and recent evidence suggests that low, non-toxic concentrations of such a compound have indeed anti-inflammatory effects. LiCl is a white cubic crystalline material. It is soluble in water, ethanol, acetone, pyridine and nitrobenzene.

The present inventors have discovered that fruiting body development in mushrooms can be regulated by modulating GSK-3 expression and/or activity: suppression of GSK-3 expression and/or activity can promote the growth of mycelium and inhibit the fruiting body formation, whereas enhancement of GSK-3 expression and/or activity can achieve opposite effects. Regulation of GSK-3 in this nature can be applied in the manufacturing of mycelium materials, which can shorten the production cycle, reduce the cost for maintenance of mycelium materials, and therefore achieve a higher level of cost-effectiveness.

BRIEF SUMMARY OF THE INVENTION

The invention relates to novel methods and compositions useful for modulating fruiting body development in fungal species during an important stage of the fungal life cycle. In particular, the present inventor discovered that, by regulating the endogenous expression and activity of GSK-3 in a fungus, the normal fruiting body development in the fungus can be controlled as well, for instance, inhibited or even prevented. Thus, in the first aspect, the present invention provides a novel method for modulating fungal fruiting body development, e.g., promoting or inhibiting the development of fruiting bodies, by way of up- or down-regulating the expression and/or activity of fungal GSK-3 gene.

In some embodiments, GSK-3 activity is inhibited or abolished, resulting in fungal fruiting body development being suppressed (e.g., delayed in onset of fruiting body formation, shorter duration of mycelial growth, less extent/ number of fruiting bodies formed, or fruiting body formation entirely prevented) when compared with a control fungus that has not received any treatment for GSK-3 up- or down-regulation. In other embodiments, GSK-3 activity is enhanced, resulting in fungal fruiting body development being increased or promoted (e.g., earlier onset, longer duration of mycelial growth, more fruiting bodies in number) compared with a control fungus, which has not had its GSK-3 activity modulated.

In some embodiments, the GSK-3 genomic sequence in the fungus' genome has been altered or manipulated. For example, for one genetically modified fungus in its genome there is an exogenous sequence encoding a polynucleotide sequence that corresponds to or is complementary to a segment of the GSK-3 genomic sequence, such as encoding for a small inhibitory RNA molecule to inhibit GSK-3 expression, or encoding a second or more copy of the GSK-3 gene for increased expression; or the GSK-3 genomic sequence is truncated, such as deleted in-part or in the entirety to reduce or abolish its expression or activity altogether; or the GSK-3 genomic sequence is mutated (e.g., by mutations such as insertions or deletions or substitutions) either in its coding region such that it encodes a protein product with altered (which could be increased or decreased or zero) GSK-3 activity or in non-coding regions such as promoter or other regulatory elements of the GSK-3 genes such that GSK-3 expression is enhanced, reduced, or abolished completely. In a transient system, the expression of endogenous GSK-3 may be modulated by way of transiently expressing a small inhibitory RNA molecule (to suppress or prevent endogenous GSK-3 expression) or a second or more copy of GSK-3 coding sequence (to increase GSK-3 expression beyond the endogenous level) by an exogenous expression cassette, which is not incorporated into the fungal cell genome. Similarly, transient expression of other GSK-3 activators or inhibitors can be used to modulate GSK-3 expression and/or activity in fungal cells.

In some embodiments, the fungus has been administered a GSK-3 inhibitor or enhancer. For example, the inhibitor or enhancer in an adequate amount is administered by injection into the fungus or is placed in a substrate or medium the fungus is exposed to or has grown in, or the inhibitor or enhancer is applied (e.g., sprayed) onto the target fungus or otherwise made contact with the fungus. In some embodiments, the GSK-3 inhibitor or enhancer is dissolved in a liquid (e.g., aqueous solution), which is then applied to the fungus by way of spraying in a vaporized or aerosolized form. In some embodiments, the inhibitor is a lithium-containing compound, especially a lithium salt such as LiCl. For example, $Li^+$ in the concentration range of about 1 nM to about 1 M, or about 10 nM to about 100 mM, or about 100 nM to about 10 mM, or about 1 nM to about 10 nM, or about 10 nM to about 100 nM, or about 100 nM to about 1 mM, or about 1 mM to about 10 mM, or about 10 mM to about 100 mM, or about 100 mM to about 1 M, may be used for this purpose. In other embodiments, the inhibitor is CHIR-99021 HCl (or its variation such as CHIR-99021 trihydrochloride), and its working concentration ranges from about 0.1 nM to about 10 mM, or about 1 nM to about 1 mM, or about 10 nM to about 10 mM, or about 100 nM to about 1 mM, or about 1 nM to about 10 nM, or about 10 nM to about 100 nM, or about 100 nM to about 1 mM, or about 1 mM to about 10 mM. In some embodiments, the GSK-3 enhancer is cisplatin, e.g., in the range of about 0.1 mM to about 100 mM, or about 1 mM to about 10 mM. In some embodiments, the fungus is a basidiomycetous fungus, especially one within the order of Agaricales, such as *Coprinopsis cinerea* or *Pleurotus djamor*.

In a second aspect, the present invention provides a novel, modified fungus, especially in the form of fungal mycelium, where the GSK-3 activity in the modified fungus is altered, either negatively (e.g., inhibited, reduced/suppressed, or even completely eliminated) or positively (e.g., increased, stimulated/promoted, or enhanced), compared to a unmodified fungus of the same species.

In some embodiments, the GSK-3 expression and/or activity in the fungus is inhibited and its fruiting body development is inhibited or reduced compared with a control fungus that has not been modified or treated to regulate GSK-3 expression and/or activity. In other embodiments, the GSK-3 expression and/or activity in the fungus is enhanced and its fruiting body development is increased compared with a control fungus that has not been modified or treated to regulate GSK-3 expression and/or activity. In some embodiments, the GSK-3 expression and/or activity in the fungus is altered by genetic manipulation or application of a GSK-3 inhibitor or enhancer. The possible means for genetic manipulation include various mutations of genomic sequence, expression of one or more exogenous sequences, are described in the above and other sections of this disclosure. In some embodiments, the GSK-3 enhancer is cisplatin. In some embodiments, the fungus is a basidiomycetous fungus, especially one within the order of Agaricales, such as *Coprinopsis cinerea* or *Pleurotus djamor*.

In a related aspect, the present invention provides a composition comprising the modified/treated fungus described above and herein, especially in the form of fungal mycelium, plus at least one substrate or medium in which the fungus has grown. In some embodiments, the substrate or medium comprises a GSK-3 inhibitor or enhancer. In some embodiments, the inhibitor is a lithium-containing compound, especially a Li salt such as LiCl. In other embodiments, the inhibitor is CHIR-99021 HCl or CHIR-99021 trihydrochloride. In some embodiments, the GSK-3 enhancer is cisplatin, e.g., in the range of about 0.1 mM to about 100 mM, e.g., about 1 mM to about 50 mM, about 5 mM to about 25 mM, about 10 mM to about 20 mM, about 1 mM to about 10 mM, about 10 mM to about 100 mM.

In a third aspect, the present invention provides a method for identifying compounds that are capable of modulating fungal fruiting body development by way of modulating GSK-3 expression (at mRNA level or at protein level) and/or activity in a fungus. The method includes the steps of: (1) contacting a fungus with a candidate compound; (2) determining GSK-3 expression or activity level in the fungus; (3) comparing the GSK-3 expression or activity level obtained in step (2) with GSK-3 expression or activity level obtained from a control fungus not contacted with the compound and detecting an increase or a decrease; and (4) identifying the compound as a modulator of fungal fruiting body development. Optionally, after detecting an increase or a decrease in step (3), a further step (5) is performed to detect changes in fruiting body development in the fungus in comparison with a control fungus that has not been contacted with the compound.

In some embodiments, an increase is detected in step (3) and the compound is identified as a GSK-3 enhancer. In other embodiments, a decrease is detected in step (3) and the compound is identified as a GSK-3 inhibitor. In some embodiments, in step (1) the fungus is injected with the compound or is exposed to the compound in a substrate or medium in which the fungus has grown or the fungus is directly applied (e.g., sprayed) with the compound on the surface of fungus or otherwise exposed to the compound in an adequate amount. In some embodiments, the fungus is a basidiomycetous fungus, especially one within the order of Agaricales, such as *Coprinopsis cinerea* or *Pleurotus djamor*.

DEFINITIONS

Figure 1:
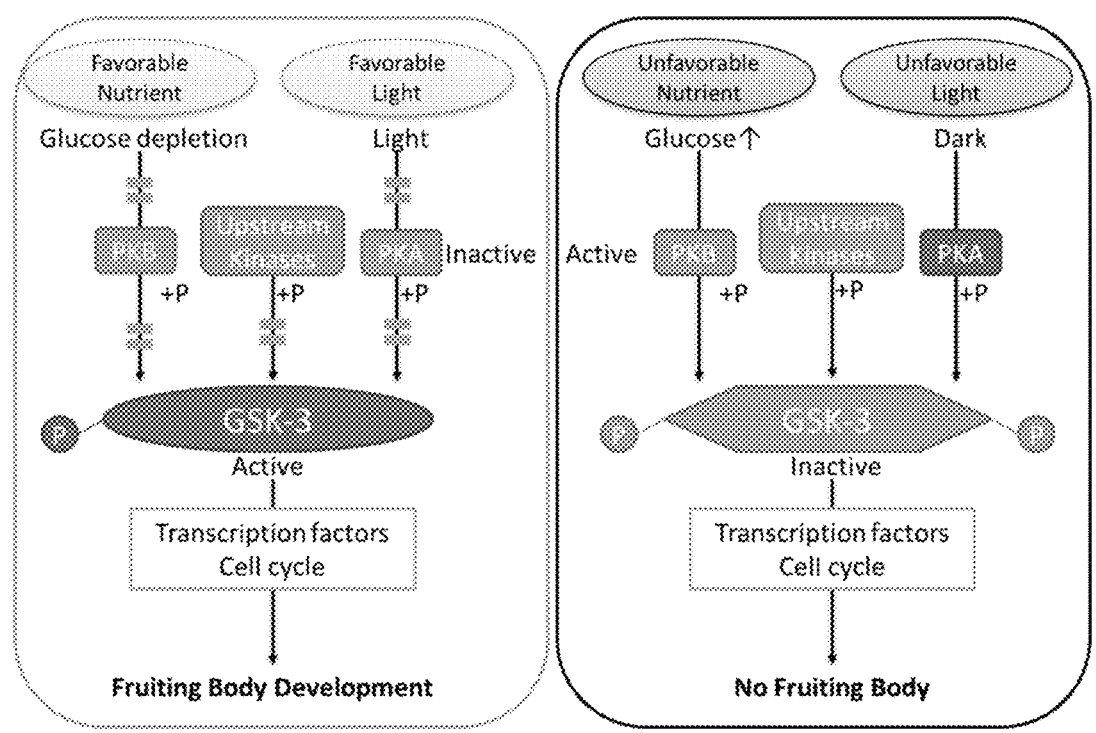
FIG. 1: Glycogen synthase kinase-3 (GSK-3) is a serine/threonine protein kinase having a monomeric structure and a size of approximately 47 kilo daltons. The gene encoding GSK-3 is highly conserved across diverse phyla. GSK-3 has important role in cell-fate specification, leading to cell differentiation or apoptosis or development through number of signaling pathways. GSK-3 could be the links between environmental stimuli and the responsive development, and a master-switch of fruiting body formation. The activity of GSK-3 determines the fruiting body development.

The term "inhibiting" or "inhibition," as used herein, refers to any detectable negative effect on a target biological process, such as RNA/protein expression of a target gene, the biological activity of a target protein, cellular signal transduction, cell proliferation, and the like. Typically, an inhibition is reflected in a decrease of at least 10%, 20%, 30%, 40%, 50%, 60%, 70%, 80%, 90% or greater in the target process (e.g., expression or activity of GSK-3, GSK-3-mediated signaling, or fungal fruiting body development), or any one of the downstream parameters mentioned above, when compared to a control. "Inhibition" further includes a 100% reduction, i.e., a complete elimination, prevention, or abolition of a target biological process or signal. The other relative terms such as "suppressing," "suppression," "reducing," and "reduction" are used in a similar fashion in this disclosure to refer to decreases to different levels (e.g., at least 10%, 20%, 30%, 40%, 50%, 60%, 70%, 80%, 90% or greater decrease compared to a control level) up to complete elimination of a target biological process or signal. On the other hand, terms such as "activate," "activating," "activation," "increase," "increasing," "promote," "promoting," "enhance," "enhancing," or "enhancement" are used in this disclosure to encompass positive changes at different levels (e.g., at least 10%, 20%, 30%, 40%, 50%, 60%, 70%, 80%, 90%, 100%, 200%, or greater such as 3, 5, 8, 10, 20-fold increase compared to a control level) in a target process or signal.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

The term "amino acid" refers to naturally occurring and synthetic amino acids (including both D- and L-amino acids), as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

There are various known methods in the art that permit the incorporation of an unnatural amino acid derivative or analog into a polypeptide chain in a site-specific manner, see, e.g., WO 02/086075.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

The term "effective amount," as used herein, refers to an amount that produces a desired effect (e.g., an inhibitory effect on fungal fruiting body development) for which a substance (e.g., a GSK-3 inhibitor) is used or administered. The effects include the prevention, inhibition, or delaying of any pertinent biological process especially fungal fruiting body development to any detectable extent. The exact amount will depend on the nature of the substance (active agent), the manner of use/administration, and the purpose of the application, and will be ascertainable by one skilled in the art using known techniques as well as those described herein.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter.

The term "GSK-3 knockdown," as used herein, describes a fungal cell that has been modified, especially genetically modified, and therefore exhibits inhibited GSK-3 expression and/or activity in comparison with the unmodified parent cell. GSK-3, or glycogen synthase kinase-3, is a serine/threonine kinase of the GSK family, which is among the 9 highly conserved kinase families of the kinase CMGC group. The amino acid sequence and corresponding polynucleotide coding sequence for *C. cinerea* GSK-3 are provided in GenBank Accession Numbers XP_001833585 (strain okayama7 #130) and NW_003307543.1 (Genomic Sequence in strain Okayama7 #130)/ jgi|Copci_AmutBmut1|363162|e_gw1.29.187.1 (in strain #326, Taxonomy ID: 1132390 and Accession: PRJNA258994), respectively. Other fungal species of Basidiomycota, including *G. lucidum, Ganoderma sinense, Ganoderma lingzhi, Pleurotus ostreatus*, and *Pleurotus citrinopileatus*, and *Pleurotus djamor* are also appropriate for generating GSK-3 knockdowns for use in practicing the methods of this invention. In particular, *Coprinopsis cinerea* and *Pleurotus djamor* are two fungal species not only within the same family of Basidiomycota but also within the same order of Agaricales. The GSK-3 is highly conserved in protein sequence. The homologous proteins include PIL30457. J in *Ganoderma sinense* ZZ0214-1, and jgi|Gansp1|158466|gm1.11165_g in *Ganoderma* sp. 10597 SS1 (North American isolate of *G. lucidum*), and KDQ33621 in *Pleurotus ostreatus* PC15. As used herein, a GSK-3 protein encompasses both *C. cinerea* GSK-3 protein and its homologs/orthologs in fungal species, especially those of Basidiomycota, having at least 90%, 91%, 92%, 93%, 94%, 95%, 96%, 97%, 98%, 99% or more sequence homology to *C. cinerea* GSK-3 protein sequence and share essentially the same biological or enzymatic activity. An example of such homolog is *Pleurotus djamor* GSK-3 protein. A GSK-3 knockdown cell is one that has been modified to have endogenous GSK-3 expression or activity level reduced by at least 20%, 25%, 30%, 50%, 75%, 80%, 90% or more in comparison with a control cell (a parent cell that has not undergone the same modification, e.g., a wild-type *Coprinopsis cinerea* or *Pleurotus djamor* cell). In some cases, the GSK-3 knockdown cell has a suppressed level of GSK-3 expression and/or activity but retains a detectable residual expression/activity. In other cases, the GSK-3 knockdown cell will have no detectable expression or activity of GSK-3. Due to the suppressed or abolished GSK-3 expression and activity, a GSK-3 knockdown fungus either is incapable of developing fruiting body or exhibit significantly reduced or delayed fruiting body development.

As used here, the term "fruiting body" refers to a multi-cellular structure of a fungus, which is also known as "sporocarp" and has spore-producing components for dispersing spores. The development of fruiting body is one stage of a fungal life cycle, a sexual phase, in contrast to the rest of fungal life cycle, characterized as vegetative mycelial growth and asexual spore production. Fruiting bodies are "epigeous" when they protrude from the ground (e.g., mushrooms growing above the ground) and are "hypogeous" when they grow underground (e.g., truffles).

As used herein, the term "about" denotes a range of value that is +/−10% of a specified value. For instance, "about 10" denotes the value range of 9 to 11.

DETAILED DESCRIPTION OF THE INVENTION

I. Introduction

The invention provides a novel approach to regulate (e.g., positively by promoting or negatively by suppressing) the fruiting body development from the living fungal mycelium by way of manipulating the expression and/or activity of GSK-3. Inhibition (including delaying onset, reducing the extent, or abolishing completely) of fruiting body development, for example, achieved by inhibiting GSK-3, can be a valuable meaning for producing a stable living mycelium-based material. On the other hand, enhanced GSK-3 expression/activity leads to hastened or prolonged fruiting in fungal mycelium. Thus, the present invention provides new methods for regulating the growth of fungal mycelium and for regulating the development of fruiting bodies. Living fungal mycelium with suppressed or abolished fruit-forming ability is a self-healing substance particularly valuable material for further engineering and development in applications such as monitoring/sensing environmental changes and secreting signals. The ability to suppress fungal fruiting is also a useful tool for maintaining stability (e.g., shape, form) of a mycelium-based material with ease and lower cost.

II. General Recombinant Technology

Basic texts disclosing general methods and techniques in the field of recombinant genetics include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994). For transformation of fungal cells, see, e.g., Ruiz-Diez, *J. Appl. Microbio.*, 2002, 92, 189-195.

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Purification of oligonucleotides is performed using any art-recognized strategy, e.g., native acrylamide gel electrophoresis or anion-exchange HPLC as described in Pearson & Reanier, *J. Chrom.* 255: 137-149 (1983).

The sequence of a gene of interest, a polynucleotide encoding a polypeptide of interest, and synthetic oligonucleotides can be verified after cloning or subcloning using, e.g., the chain termination method for sequencing double-stranded templates of Wallace et al., *Gene* 16: 21-26 (1981).

III. Modulating GSK-3 Expression and Activity

The present inventors discovered that GSK-3 activity directly correlates with the development of fruiting bodies in fungi, especially basidiomycetous fungi such as *C. cinerea*. By regulating GSK-3 expression and activity, one can regulate fungal fruiting body development. Thus, the present disclosure provides an innovative strategy for easy, reliable, and low cost maintenance of material containing live fungal mycelium.

A. Inhibition or Suppression of GSK-3 Expression and/or Activity

1. Genetic Manipulation

A variety of different methods are suitable for inhibiting or suppressing GSK-3 expression and/or activity level in fungi. One possibility is to reduce or abolish GSK-3 expression by genetic manipulation of the fungal cells' genomic sequence encoding the GSK-3 protein or by transient or permanent expression of small inhibitory RNAs. Another possibility is to suppress the activity of endogenously expressed GSK-3 protein by introducing a GSK-3 inhibitor into the external environment in which the fungi grow.

A GSK-3 knockdown cell may be generated by genetic manipulation of the genomic GSK-3 sequence of a suitable parent cell. Methods such as sequence homology-based gene disruption methods utilizing a viral vector or CRISPR system can be used for altering the GSK-3 genomic sequence, for example, by insertion, deletion, or substitution, which may occur in the coding region of the gene or in the non-coding regions (e.g., promoter region or other regulatory regions) and which may result in complete abolition of GSK-3 expression, reduced GSK-3 expression, or unaltered expression at mRNA level but diminished GSK-3 protein activity.

Alternatively, GSK-3-knockdown cells may be generated by introducing into suitable parent cells an exogenous expression cassette encoding (1) one or more polynucleotide sequence that can interfere with or inhibit the expression of the endogenous GSK-3 gene at mRNA level; or (2) a protein that can suppress the activity of GSK-3 protein. For instance, a vector (such as a viral vector based on a viral genome structure) comprising at least one coding sequence for an siRNA, a microRNA, a miniRNA, a lncRNA, or an antisense oligonucleotide that is capable of disrupting GSK-3 expression at the mRNA level may be used. Typically, such coding sequence corresponds to or is complementary to a segment of the GSK-3 genomic sequence. As another possibility, the vector may introduce into the recipient cell one or more coding sequence encoding for a protein product that interferes with the biological activity of GSK-3 and thus acts as an inhibitor of GSK-3 protein. Some examples of such protein inhibitors include a neutralizing antibody against GSK-3, a peptide that can bind and inactivate the GSK-3 protein, or a dominant negative mutant of the GSK-3 protein. Any of the above-described exogenous sequences may be transiently present in a recipient cell or may be integrated into the recipient cell's genome thus present in a permanent manner. For general techniques in transferring genetic material into fungal cells, see, e.g., Ruiz-Diez, *J. Appl. Microbio.*, 2002, 92, 189-195.

Upon introduction of the exogenous polynucleotide sequence(s) into parent cells, the cells can be screened for evidence of suppressed GSK-3 expression and/or activity. Various assays including polynucleotide detection assays (e.g., PCR or RT-PCR), immunological assays (e.g., western blot), and GSK-3 functional assays may be performed to identify desirable transformants exhibiting significantly diminished or abolished GSK-3 expression and/or activity. Ideally, the level of decrease in GSK-3 expression and/or activity is at least a 10% decrease compared to unmodified parent cells; more preferably, the decrease is at least 20%, 30%, 40%, 50%, 60%, 70%, 80%, 90%, or 95% or even greater including complete elimination.

2. Direct Application of GSK-3 Inhibitors

In addition, suppression of GSK-3 expression and/or activity in a fungus may be achieved by applying an inhibitor of GSK-3 gene expression or an inhibitor of GSK-3 protein activity in the external environment where the fungus grows. Often, when an inhibitor is applied in a substrate or medium used to grow the fungus, the inhibition on GSK-3 is transient and reversible: the inhibition is in place when the inhibitor is present, whereas the inhibition is lifted once the inhibitor is removed, e.g., being adequately washed away or diluted from the substrate or medium. Known inhibitors of GSK-3 include lithium-containing compounds, especially lithium salts such as LiCl, as well as compounds of other chemical nature such as CHIR-99021 HCl or its variations such as CHIR-99021 trihydrochloride. For example, Li containing compounds in the concentration range of about 1 nM to about 1 M may be used for this purpose. CHIR-99021 trihydrochloride is another known GSK-3 inhibitor (CAS Number: 1782235-14-6; Chemical Name: 6-[[2-[[4-(2,4-Dichlorophenyl)-5-(5-methyl-1H-imidazol-2-yl)-2-pyrimidinyl]amino]ethyl]amino]-3-pyridinecarbonitrile trihydrochloride, available through commercial suppliers such as ApexBio, Tocris, and Sigma-Aldrich) and can be used in the concentration range of about 0.1 nM to about 10 mM. Other known GSK-3 inhibitors include: Maleimide Derivatives; Staurosporine and Organometallic Inhibitors; Indole Derivatives; Paullone Derivatives; Pyrazolamide Derivatives; Pyrimidine and Furopyrimidine Derivatives; Oxadiazole Derivatives; Thiazole Derivatives; and Miscellaneous Heterocyclic Derivatives. In addition, previously unknown GSK-3 inhibitors can be identified according to the screening methods described herein and can be used for practicing this invention, e.g., for suppressing fungal fruiting body development.

B. Enhancing GSK-3 Expression or Activity

1. Nucleic Acids Encoding GSK-3 Protein

Enhancement of GSK-3 gene expression can be achieved through the use of nucleic acids encoding a functional GSK-3 protein. Such nucleic acids can be single-stranded nucleic acids (such as mRNA) or double-stranded nucleic acids (such as DNA) that can translate into an active form of GSK-3 protein under favorable conditions.

In one embodiment, the GSK-3-encoding nucleic acid is provided in the form of an expression cassette, typically recombinantly produced, having a promoter operably linked to the polynucleotide sequence encoding the GSK-3 protein. The promoter may be one that is normally found in fungal cells directing expression of native GSK-3 gene, or it may be a heterologous promoter found in nature for directing the expression of another gene, other than the GSK-3 gene. Administration of such nucleic acids can increase the GSK-3 protein expression in the target recipients, e.g., fungal cells. Since the GSK-3 sequence encoding its mRNA is known in fungal species, for example, C. cinerea, one can derive a suitable GSK-3-encoding nucleic acid from the sequence, species homologs/orthologs, and variants of these sequences.

2. GSK-3 Proteins

By directly administering an effective amount of an active GSK-3 protein to fungal cells, the total GSK-3 activity may also be effectively increased. For example, this can be achieved by administering (e.g., by injection) a recombinantly produced GSK-3 protein possessing its biological activity to the target fungal cells in order to increase GSK-3 activity and promote fruiting body formation.

3. Activators of GSK-3 Protein Expression and/or Activity

Increased GSK-3 protein activity can be achieved with an agent that is capable of up-regulating the expression of endogenous GSK-3 protein or enhancing the activity of endogenous GSK-3 protein. In some cases, an activating agent may be added into the medium or substrate in which a fungus grows, such that the activation is reversible in nature. Activating agents may include transcriptional activators specific for the GSK-3 promoter and/or enhancer. Such activating agents can be screened for and identified using the GSK-3 expression assays known in the art and described in the examples herein. One exemplary activator or enhancer of GSK-3 is cisplatin, also known as cisplatinum, platamin, neoplatin, cismaplat, or cis-diamminedichloridoplatinum(II) (CDDP), a chemical most commonly used in chemotherapy in cancer treatment.

Activators or agonists of the GSK-3 protein act by enhancing the biological activity of the GSK-3 protein, typically (but not necessarily) by direct binding with the GSK-3 protein and/or its interacting proteins. Preliminary screening for such agonists may start with a binding assay for identifying molecules that physically interact with the GSK-3 protein, e.g., in a cell-free assay system or within a cell expressing the GSK-3 protein.

IV. Modified Fungi with Controlled Fruiting Body Development Profile

The present invention also provides a live fungal mycelium that exhibits an altered and more desirable profile of fruiting body development as well as compositions that contain the fungal mycelium. For example, in many instances one would prefer for a live fungal mycelium to refrain from developing fruiting bodies such that the mycelium is easily maintained without concerns of loss in its shape, form, or consistency. In contrast to the currently-in-use method of heat-killing fungal mycelium to prevent fruiting body formation, a live version of mycelium that simply does not form fruiting bodies is far more desirable considering its live nature and thus healing potential.

In other cases, promoting fruiting body development may be of interest. For instance, when the intended goal is to produce and harvest as many fruiting bodies (e.g., mushrooms and truffles) as possible in a defined time period, having enhanced fruiting body development is beneficial.

For producing a live fungal mycelium with an enhanced or inhibited fruiting body development profile, either a permanent means (e.g., GSK-3 knockdown or GSK-3 knockout fungal strain) or a transient means (e.g., application of an activator or inhibitor of GSK-3 present in the medium for fungi) can be employed. While the former may be easier to maintain in the long term, efforts involved in the initial stage of establishing the genetically modified fungal strains are tremendously more significant both in cost and in time. In contrast, the latter offers the benefits of flexibility and low-cost use, when the GSK-3 activator or inhibitor can be readily removed at an appropriate time such that the fungus may resume its normal life cycle of different phases.

V. Methods for Identifying GSK-3 Modulators

The present invention also provides screening methods for identifying compounds that are capable of modulating GSK-3 expression and/or activity in fungi. As described above, these GSK-3 modulators are useful for regulating the fruiting body development characteristics of fungi; for example, a GSK-3 inhibitor can be used to delay or abolish fruiting body formation, whereas a GSK-3 enhancer can be used to promote or enhance fruiting body formation.

A first screening method focuses on the direct effect of a candidate compound on GSK expression and/or activity. More specifically, a fungus is first contacted with a candidate compound; GSK-3 activity level in the contacted fungus is then determined quantitatively; the GSK-3 activity level so obtained is compared with GSK-3 activity level obtained from a control fungus not contacted with the compound (control level) to detect an increase or a decrease from the control level; and lastly, a candidate compound is identified as a modulator of fungal fruiting body development when there is an increase or decrease: an increase indicates the compound as a GSK-3 enhancer, whereas a decrease indicates the compound as a GSK-3 inhibitor.

There are various means for contacting the fungus with a candidate compound: injection of the compound into a fungus is one possibility, whereas placing the compound in the environment (e.g., a substrate or medium) where the fungus grows is another possibility.

Upon preliminarily determining a candidate compound being a GSK-3 modulator, it is optionally subject to further testing and verification, for example, by applying the compound to a fungus and monitor its fruiting body development characteristics. Changes in fruiting body formation confirms the compound's status as a GSK-3 modulator.

A second screening method focuses on the physical interaction between a modulator and GSK-3 protein. In many although not all cases, a compound that modulates the activity of a protein by directly interacting with the protein. As such, an in vitro or cell-free screening method effective for providing a preliminary indication of whether a molecule is a GSK-3 modulator relied on the detection of physical interaction between a candidate compound and the GSK-3 protein. In particular, a candidate compound is first placed together with the GSK-3 protein under conditions generally allowing protein-protein binding (e.g., in an aqueous solution with appropriate salts and pH), the physical association between the candidate compound and the GSK-3 protein is then detected and quantitatively measured. If an increased level of association is observed, especially in comparison with the association level between the GSK-3 protein and another control compound known to not physically interact/bind with GSK-3 protein, the candidate compound is preliminarily deemed a modulator of GSK-3 protein. Optionally, the compound may be subject to further testing and verification, for example, in cell-based assays, by detecting its potential effects on GSK expression or activity in fungal cells and/or fruiting body formation in fungi.

EXAMPLES

The following examples are provided by way of illustration only and not by way of limitation. Those of skill in the art will readily recognize a variety of non-critical parameters that could be changed or modified to yield essentially the same or similar results.

Introduction

The present invention provides a novel approach using an inhibitor of GSK-3 kinase activity, such as lithium chloride, LiCl, to fungal mycelium (or to the substrate for mycelium growth) sufficient to regulate the mycelium growth and inhibit or prevent fruiting body formation.

In one example, 3 g/L LiCl is mixed in the substrate to grow C. cinerea mycelium. Treatment of LiCl resulted in acceleration in mycelium growth rate, absence of fruiting body and general decrease in GSK-3 gene expression.

Thus, methods of the invention inhibit or prevent fruiting body formation in the living mycelium based material as shown in the Examples that follow, wherein the appearance of fruiting body was inhibited in cultured mycelium treated with lithium. This is the first report of using a GSK-3 inhibitor, such as lithium or any other GSK-3 inhibitor, to suppress or abolish fruiting body formation in living fungal material.

Materials and Methods

In order to validate the GSK-3's function in fruiting body development in C. cinerea, a GSK-3 inhibitor was first used to regulate the activity of GSK-3. All strains used are derivatives of C. cinerea AmutBmut #326 strain. C. cinerea is cultured on YMG (Yeast extract, malt extract and glucose) agar plates at 37° C. for about 1 week until mycelia grow over the whole agar surface. Fruiting body development is induced by incubating the mycelia at 25° C. under a light/dark cycle.

Figure 2:
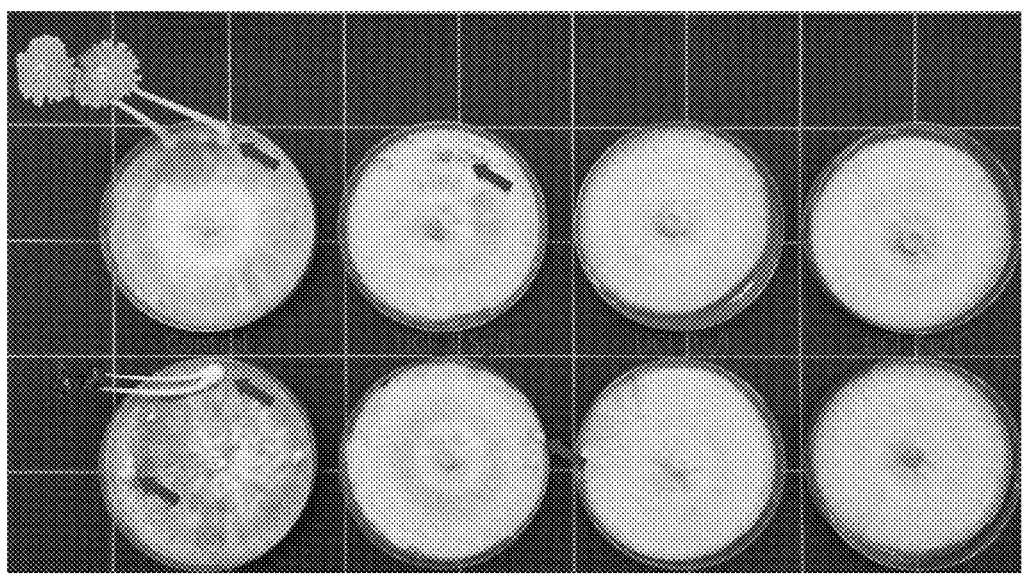
FIG. 2: The development of *C. cinerea* treated with different doses of LiCl. *C. cinerea* were cultivated on YMG agar at 37° C. till mycelia reached the edge of agar, and then 2 ml LiCl ($H_2O$) solution were added under the agar and the plates were transferred to the condition of 12 h light/12 h dark cycle under 25° C. After 8 days, mature fruiting bodies, young fruiting bodies, primordia and initials were produced in the control group, while the 1.5 g/L LiCl treated group produced only initials and primordia. No initiation was observed in the groups treated with higher concentration of LiCl, in the following 30 days.

Two methods have been tested to deliver LiCl (Sigma-Aldrich, St. Louis, Mo., USA). One delivery method is to mix LiCl in the agar mixture before autoclave sterilization, and the other method is to add 2 ml LiCl solution under the agar, after mycelia reaches the petri dish edge. LiCl treatments inhibited the fruiting body initiation in a dose-dependent manner (FIG. 2). Given that LiCl is a specific inhibitor to GSK-3, it is understood that GSK-3 plays a key role in fruiting body development signaling in C. cinerea.

TABLE 1

Effect of GSK-3 inhibitor on C. cinerea development

| | Effect on Mycelium growth | | | | Effect on Fruiting body development | | | |
|---|---|---|---|---|---|---|---|---|
| | 1.5 g/L | 3 g/L | 6 g/L | ddH$_2$O | 1.5 g/L | 3 g/L | 6 g/L | ddH$_2$O |
| LiCl in agar | Acceleration | Acceleration | Retarded growth | normal | No initiation | No initiation | No initiation | normal |
| LiCl under agar* | — | — | — | — | Retarded initiation | No initiation | No initiation | normal |

Figure 3:
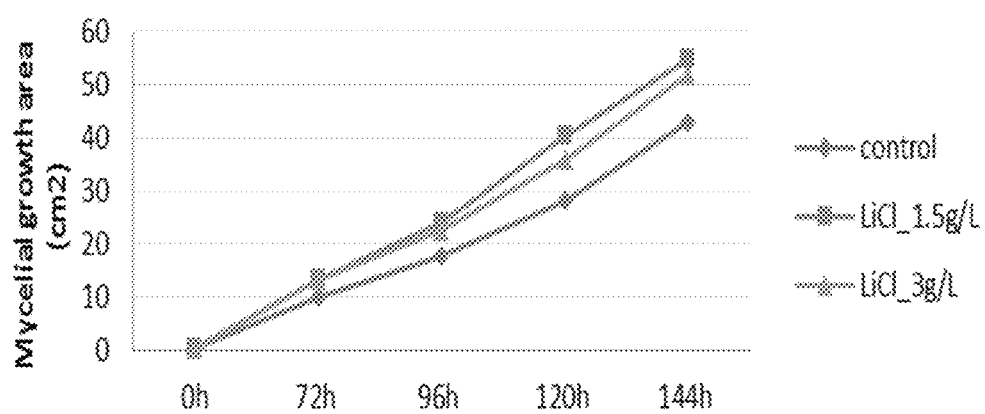
FIG. 3: Mycelial growth of *C. cinerea* with different doses of LiCl, biological triplicates were used for mean calculation. The growth rate of mycelium treated with 1.5 g/L and 3 g/L LiCl is higher than control.
Figure 4:
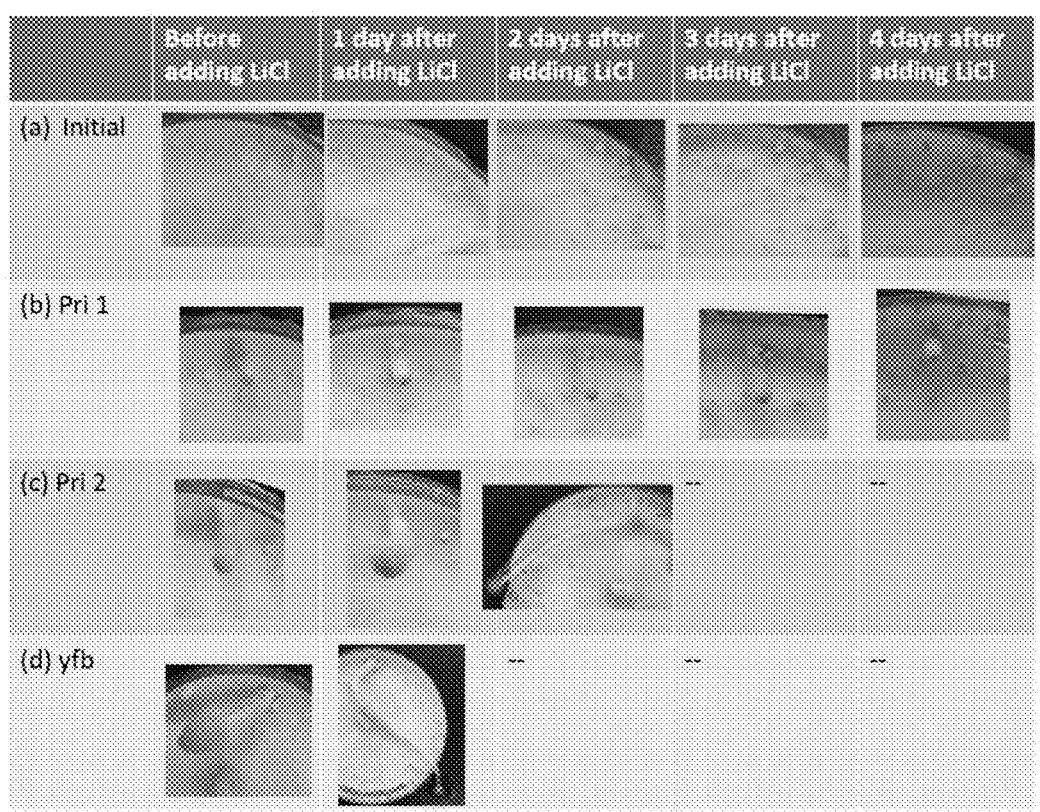
FIG. 4: The development of *C. cinerea* treated with 0.1 ml of 3 g/L LiCl at different stage. Adding 3 g/L LiCl at (a) initial and (b) primordium 1 led to inhibition on further development. Adding 3 g/L LiCl at (c) primordium 2 and (d) young fruiting body cannot inhibit the fruiting body development.
Figure 5:
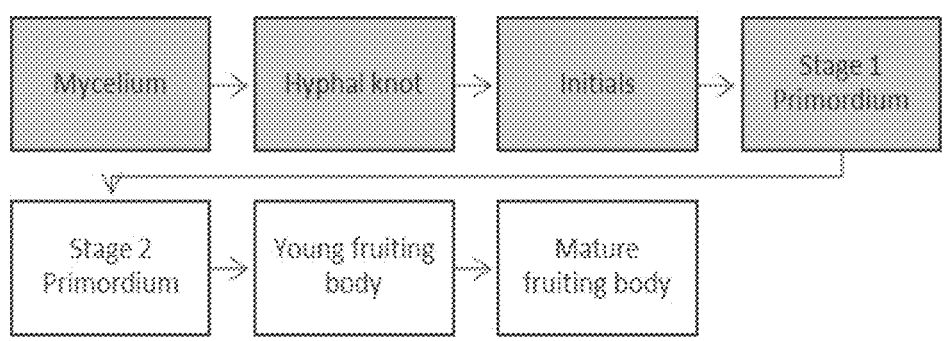
FIG. 5: Life cycle of the mushroom-forming fungi, and the sensitive windows to the GSK-3 inhibitors (stages in grey). Intervention of LiCl at stages of mycelium, hyphal knot, initiation and stage-1 primordium resulted in arrestment in fruiting body development. These stages are sensitive windows.
Figure 6:
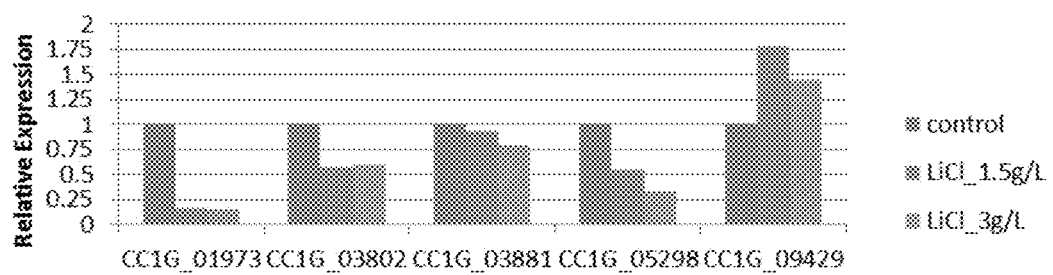
FIG. 6: The gene expression levels are indicated by the abundance of segments on the cDNA, by real-time PCR. The GSK-3 and its target genes change the expression level under LiCl treatment. Glycogen synthase (CC1G_01973); GSK-3 protein kinase (CC1G_03802); eukaryotic translation initiation factor 1 (CC1G_03881); Uncharacterized protein with Ricin B-type lectin domain (CC1G_05298); Translation initiation factor eIF2 gamma subunit (CC1G_09429).
Figure 7:
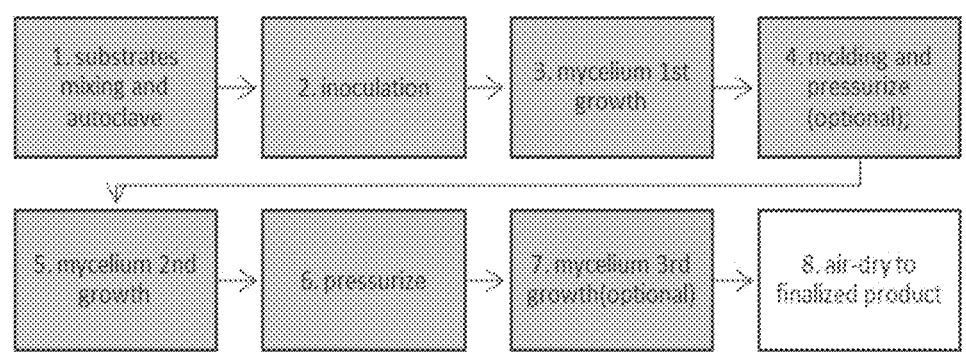
FIG. 7: Basic procedures of the production pipeline of living mycelium-based materials, where the GSK-3 inhibitors can be added at any time from procedure 1 to 7.
Figure 8:
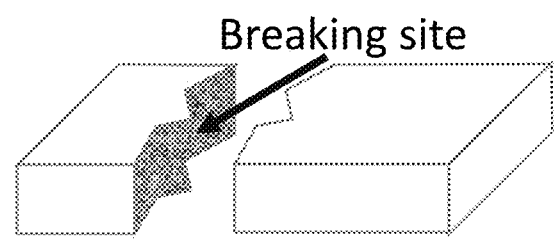
FIG. 8: Comparison of the self-healing ability between the mycelium blocks treated by heating and LiCl. The two group of mycelium blocks (e.g., *Pleurotus* djamor blocks) were broken in the middle. In each group, 3 blocks were spread with the solution of YMG broth and the other 3 blocks with dd$H_2O$ on the broken sites. The two parts of one block were incubated together for 3 days. The results show that the block treated with LiCl can self-repair and rebuild the bindings by the new hyphae.

*The LiCl concentration was calculated with the volume of sum of agar and H$_2$O The mycelial growth rate was measured for the LiCl treated C. cinerea. Biological triplicates were cultivated on YMG agar plates at 37° C. in darkness, treated with different doses of LiCl. The mycelium growth was recorded for 4 days. FIG. 3 shows the average growth rate of each group. The results show that the optimal concentrations of LiCl can accelerate the mycelium growth, while the 6 g/L LiCl inhibit the growth of mycelium (details are shown in Table 1).

Lithium has mycelium-enhancing effect to some mushroom forming fungi, but the concentration range of such effect is narrow. In some other mushroom forming fungi, high concentration of LiCl may inhibit the mycelium growth, especially in Trichoderma species, which is a common contamination of the edible mushroom (H. G. Wildman 1991). Thus, while LiCl might be applied to prevent fruiting in some mushroom-forming fungi, it can also inhibit the contamination during manufacturing in some scenario.

The development of fruiting bodies was observed for LiCl treated C. cinerea. After 8 days, mature fruiting bodies, young fruiting bodies, primordia and initials were produced in the control group, while the 1.5 g/L LiCl treated group produced only a few initials and stage 1 primordia. No initiation was observed in the groups treated with higher concentration of LiCl, in the following 30 days. This result is consistent with Pleurotus eryngii, which cannot form fruiting body when cultivated with lithium carbonate higher than 0.75 mM in a nutrition fortification study (Mleczek et al. 2017). The results show that the species-specific concentrations of lithium can inhibit/block the fruiting body development.

Moreover, other agents that specifically target GSK-3, can also prevent the development of fruiting body. Therefore, it can be concluded that the effect of lithium is mediated through the inhibition of GSK-3 activity. In support of this conclusion: 1) CHIR-99021 HCl, an alternative GSK-3 inhibitor that acts through a distinct mechanism, also inhibits fruiting body formation; 2) RNAi mediated depletion of GSK-3 blocks fruiting body formation; 3) putative GSK-3 null mutants cannot develop fruiting bodies.

The effect of LiCl at different developmental stages of C. cinerea were tested. 0.1 ml of 3 g/L LiCl were added to the agar plate. Adding 3 g/L LiCl at initial and stage-1 primordium led to the arrest of their development, while stage-2 primordium and young fruiting body could continue to develop into fruiting bodies. Intervention of LiCl at stages of hyphal knot, initiation and stage-1 primordium resulted in arrestment in fruiting body development.

The sensitive window to LiCl is from mycelium, hyphal knot, initial to primordium. This indicates that the LiCl may inhibit fruiting through affecting the cell differentiation. Inhibitors of GSK-3 were shown to maintain the mouse and human embryonic stem (ES) cells in undifferentiated status, while removing inhibitor promotes differentiation into multiple cell lineages (Kirby et al. 2012). The potency maintaining function of GSK-3 may be related to protein degradation. After phosphorylated by GSK-3, many substrates will then be targeted by ubiquitination for proteasome-mediated degradation. Undifferentiated cells are proliferative because GSK-3 activity is limited by persistent unfavorable growing condition signals. The effectors of GSK-3, such as transcription factors, are less modified by phosphorylation and ubiquitination, so their half-lives are prolonged to enhance stem/precursor cell proliferation (Westermarck 2010).

The expression levels of targets genes of GSK-3 were measured to explore the mechanism of LiCl. To characterize the gene expression profile changes, quantitative real-time PCR analysis was performed. the kinase and its substrates by Orthologue searching were selected. A total of 83 GSK-3 substrates reported in human and mouse were mapped to the C. cinerea genome, and 52 orthologues were identified. Among them, CC1G_01973, CC1G_03881, and CC1G_09429 were selected for real-time PCR analysis. Samples treated by different doses of LiCl were frozen and homogenized in liquid nitrogen to extract total RNAs. The results show that the LiCl could regulate the expression of the selected GSK-3 target genes, as well as the GSK-3 gene itself. eIF1 gene expression decreased with increase of LiCl concentration. Decreased eIF1 gene expression supports that LiCl block the fruiting through inhibiting GSK-3 activity in initiating the translation of key protein. Binding of eIF1 to 40S ribosome is key to maintain an open conformation on 40S ribosomal subunit to initiate translation (Passmore et al. 2007). Low level of eIF1 was also found to lower mRNA translation in Saccharomyces cerevisiae (You et al. 2010).

For practicing the methods of the invention to produce living mycelium based material, the basic production pipeline is designed for adding GSK-3 inhibitors, particularly the lithium or lithium salt. The production pipeline can be all of part of the following procedures: 1) substrates mixing and autoclave; 2) inoculation; 3) mycelium 1st growth; 4) molding and pressurize; 5) mycelium 2nd growth; 6) pressurize (optional); 7) mycelium 3rd growth (optional); 8) air-dry to finalized product. LiCl or other GSK-3 inhibitors can be added at any time from procedure 1) to 7), by mixing in the substrate before autoclave, or spraying to the mycelium after a period of growth.

The self-healing ability and stability of the living material is tested by comparison of the self-healing ability between the mycelium blocks treated by heating and LiCl. To prepare the demo mycelium blocks, water (as in group "Heat") or 2 g/L LiCl water solution (as in group "Lithium"), sawdust, wheat bran and calcium carbonate were mixed as substrate and autoclaved the substrate. Then the Pleurotus djamor was inoculated to the substrate, and incubated under 27° C. continuous dark for 7 days. Then 30 g of the mixture of mycelium and substrate were transferred into molds of block, with same volume and pressure. The blocks were incubated under 27° C. continuous dark for another 7 days. Then the blocks of "Heat" group were dried by oven, and the block of "Lithium" group were dried by dehumidifier, to the same mass of the "Heat" group.

The two group of mycelium blocks were broken in the middle. In each group, 3 blocks were spread with the solution of YMG broth and the other 3 blocks with ddH$_2$O on the broken sites. The two parts of one block were incubated together for 3 days. The results show that the blocks of "LiCl" group treated with YMG broth can self-repair and rebuild the bindings by the new hyphae, while the ones treated with ddH$_2$O have fewer new hyphae. However, the blocks of "Heat" group cannot repair themselves. The blocks from both groups were clear of initials and fruiting bodies in the following 30 days, and keep stable structure and shape. The living mycelium blocks exhibit aspects of both the inert grown materials that are being produced today at the factory scale, such as structural integrity, as well as those of living systems, such as self-repair.

Results

Example 1: Knockdown of GSK-3 Genes C. cinerea by siRNA/dsRNA

After the discovery of glycogen synthase kinase 3 (GSK-3) inhibitor, lithium chloride (LiCl), it was deduced that GSK-3 plays a key role in fruiting body development signaling in C. cinerea. For the specific validation of selected putative regulatory kinases, small interference RNA (siRNA) was then applied on C. cinerea culture by transient knockdown. Firstly, GSK-3 dsRNA (about 300 bp) was produced with gene specific primer and the kinase genes from RNA of C. cinerea. Then the GSK-3 dsRNA was digested into about 21 bp long siRNA with RNaseIII. After primordium grew into stage 2 primordium (about 8-10 mm), 5 ul GSK-3 siRNA was added into selected *C. cinerea* by needle injection. 3 controls included without any treatment, injury by needle without any injection, and injection with 5 ul water. By 3-day continuous treatment, the mature fruiting body developed from 2 stages of primordium in 3 set of controls. The transient knockdown with GSK-3 siRNA cultures produced deformed fruiting body and some showed retarded fruiting body development. When the selected primordium was treated with siRNA and retarded the growth, the primordium next to it continued fruiting body development into mature fruiting body. With the GSK-3 siRNA transient knockdown, it can be confirmed that GSK-3 plays a key role in fruiting body development signaling in *C. cinerea*.

Example 2: Effect of CHIR-99021 HCl

Another GSK-3 inhibitor was used to confirm inhibition of LiCl on GSK-3. *C. cinerea* was cultivated on YMG agar and treated with water for control group and 1 uM, 100 uM and 500 uM of CHIR-99021 HCl for experimental group. Control and 1 uM and 100 uM CHIR-99021 HCl experimental group developed initials. Higher CHIR-99021 HCl concentration inhibited fruiting.

Example 3: LiCl Clearance can Induce the Fruiting Body Formation

The LiCl inhibition of *C. cinerea* mycelium can be relieved by removing LiCl or diluting the concentration of LiCl, for example, by washing the mycelium and substrate with $ddH_2O$, or by transferring the mycelium onto a clean substrate. The inhibition is released when the LiCl concentration lowers, and the fruiting bodies develops again.

Example 4: GSK-3 Mutant Cannot Form Fruiting Body

Putative GSK-3 null mutant of *C. cinerea* was cultivated on YMG agar, but it cannot form any hyphal knots, initials or fruiting bodies.

Example 5: GSK-3 Suppression and Activation in Two Fungal Species

Two GSK3 inhibitors (LiCl and CHIR-99021 HCl) and one GSK3 activator (Cisplatin) were tested in *Coprinopsis cinerea*, and one GSK3 inhibitor (LiCl) was tested in *Pleurotus djamor* (commonly known as the pink oyster mushroom). Belonging to the same order Agaricales, these two tested mushroom species are of two different families, Psathyrellaceae and Pleurotaceae, respectively.

Figure 9:
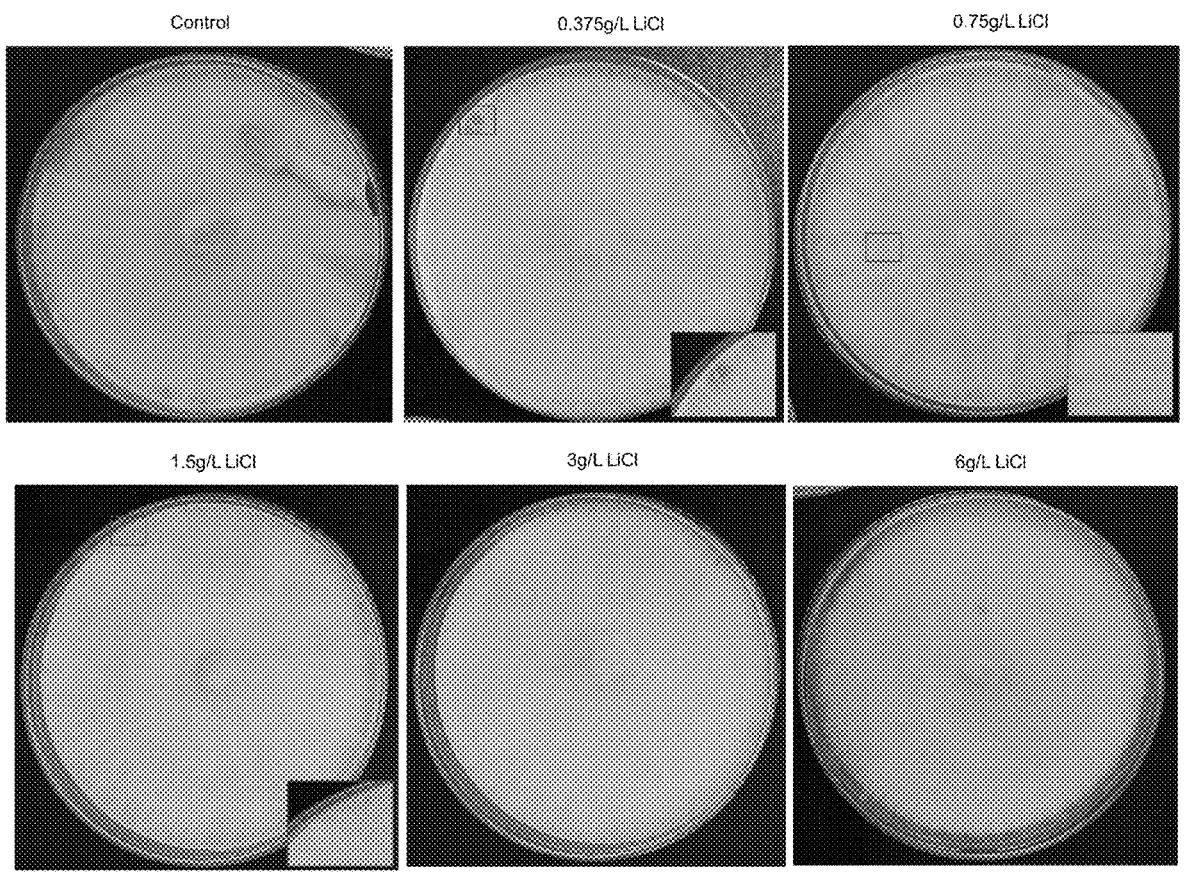
FIG. 9: Effect on *C. cinerea* fruiting body development by GSK3 inhibitor-LiCl at different concentration. Water or LiCl solution was spread on the surface of YMG agar, before inoculation. After 6-days all dark incubation in 37° C., the plates were transferred to 25° C. with 12-hours light and 12-hours dark cycle (light/dark cycle) for 5-days incubation. Young fruiting bodies developed on the control plates treated with water. Primordium were formed on the plates treated with 0.375 g/L LiCl. Initials and hyphal knots formed on the plates treated with 0.75 g/L and 1.5 g/L LiCl respectively. The plates treated with 3 g/L LiCl and 6 g/L LiCl were arrested in mycelium stage, and mycelium treated with 6 g/L LiCl stopped before reaching the edge of plates.

As shown in FIG. 9, how LiCl affects *C. cinerea* fruiting body development was tested. Water or LiCl solution was spread on the surface of YMG agar before inoculation of *C. cinerea*. After 6-days all dark incubation in 37° C., the plates were transferred to 25° C. with 12-hours light and 12-hours dark cycle (light/dark cycle) for 5-days incubation. Young fruiting bodies developed on the control plates treated with water. Primordium were formed on the plates treated with 0.375 g/L LiCl. Initials and hyphal knots were formed on the plates treated with 0.75 g/L and 1.5 g/L LiCl respectively. The plates treated with 3 g/L LiCl and 6 g/L LiCl were arrested in mycelium stage, and mycelium treated with 6 g/L LiCl stopped before reaching the edge of plates. These results showed an increasingly stronger inhibitory effect on *C. cinerea* fruiting body development by LiCl at higher concentrations.

Figure 10:
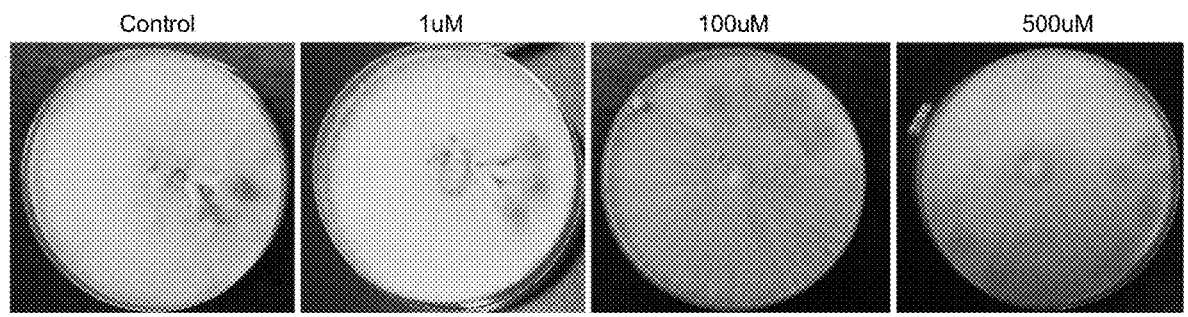
FIG. 10: Effect on *C. cinerea* fruiting body development by GSK3 inhibitor-CHIR-99021 HCl at different concentration. Water or CHIR-99021 HCl solution was spread on the surface of YMG agar, before inoculation. After the mycelium reached the edge of plates, the plates were transferred to 25° C. with light/dark cycle for 6-days incubation. Young fruiting bodies developed on the control plates treated with water and the plates with 1 µM CHIR-99021 HCl. The plates with 100 µM CHIR-99021 HCl developed primordium. The plates treated with 500 µM CHIR-99021 HCl remained in mycelium stage.

As shown in FIG. 10, how CHIR-99021 HCl affects *C. cinerea* fruiting body development was tested. Water or CHIR-99021 HCl solution was spread on the surface of YMG agar before inoculation of *C. cinerea*. After the mycelium reached the edge of plates, the plates were transferred to 25° C. with light/dark cycle for 6-days incubation. Young fruiting bodies developed on the control plates treated with water and the plates with 1 µM CHIR-99021 HCl. The plates treated with 100 µM CHIR-99021 HCl developed primordium. The plates treated with 500 µM CHIR-99021 HCl remained arrested in mycelium stage. These results showed an increasingly stronger inhibitory effect on *C. cinerea* fruiting body development by CHIR-99021 HCl at higher concentrations.

Figure 11:
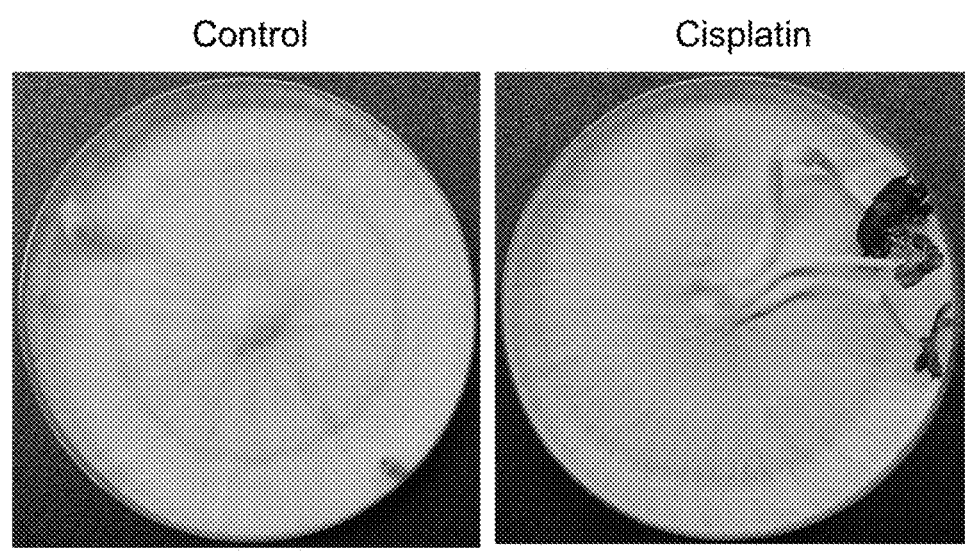
FIG. 11: Effect on *C. cinerea* fruiting body development by GSK3 activator-Cisplatin at different concentration. Water or Cisplatin solution was spread on the surface of YMG agar, before inoculation. After the mycelium reached the edge of plates, the plates were transferred to 25° C. with light/dark cycle. After 6-days incubation, the YMG plates treated with 1 ml saturated Cisplatin had fruiting body and began autolysis. Young fruiting body developed on the control YMG plates treated with water.

As shown in FIG. 11, how cisplatin affects *C. cinerea* fruiting body development was tested. Water or Cisplatin solution was spread on the surface of YMG agar before *C. cinerea* inoculation. After the mycelium reached the edge of plates, the plates were transferred to 25° C. with light/dark cycle. After 6-days incubation, the YMG plates treated with 1 ml saturated Cisplatin had fruiting body and began autolysis. Young fruiting body developed on the control YMG plates treated with water. These results showed a positive or promoting effect on *C. cinerea* fruiting body development by Cisplatin.

Figure 12:
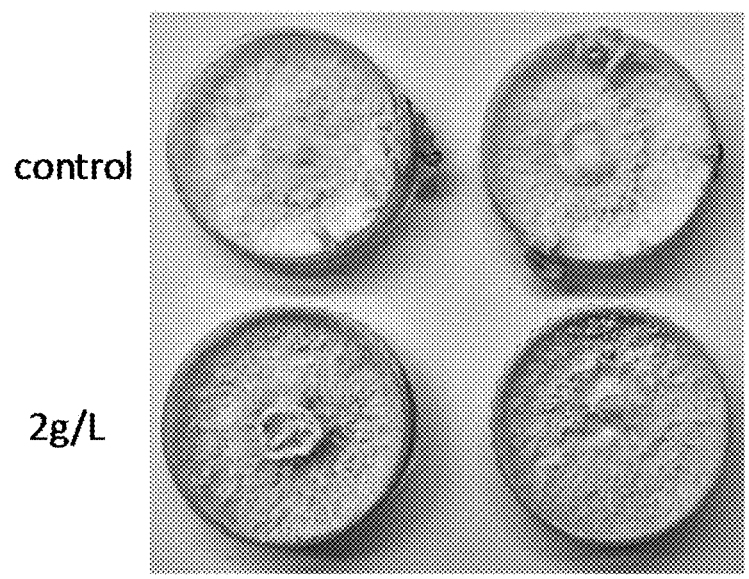
FIG. 12: Effect on *Pleurotus djamor* fruiting body development by GSK3 inhibitor-LiCl at different concentration. LiCl was added to YMG agar medium before autoclave. After 10-days all dark incubation in 27° C., the plates were transferred to 25° C. with 12-hours light and 12-hours dark cycle (light/dark cycle) for 10-days incubation. Mature fruiting bodies developed on the control plates. The plates treated with 2 g/L LiCl failed to develop fruiting body.

As shown in FIG. 12, how LiCl affects *Pleurotus djamor* fruiting body development was tested. LiCl was added to YMG agar medium before autoclave. After 10-days all dark incubation in 27° C., the plates were transferred to 25° C. with 12-hours light and 12-hours dark cycle (light/dark cycle) for 10-days incubation. Mature fruiting bodies developed on the control plates. The plates treated with 2 g/L LiCl failed to develop fruiting body. These results showed an inhibitory effect on *Pleurotus djamor* fruiting body development by LiCl.

These data unequivocally support the conclusion that among fungus species of the division Basidiomycota, especially of the order Agaricales, GSK3 inhibitors inhibit/reduce/decelerate the fruiting body formation, whereas GSK3 enhancers activate/increase/accelerate the fruiting body formation.

All patents, patent applications, and other publications, including GenBank Accession Numbers or equivalent sequence identification numbers, cited in this application are incorporated by reference in the entirety of their contents for all purposes.

REFERENCES

De Assunão, L. S. et al., 2012. Enrichment of mushrooms: An interesting strategy for the acquisition of lithium. *Food Chemistry*, 134(2), pp. 1123-1127.

H. G. Wildman, 1991. Lithium chloride as a selective inhibitor of *Trichoderma* species on soil isolation plates. *Mycological Research*, 95(12), pp. 1364-1368.

Kirby, L. A. et al., 2012. Glycogen synthase kinase 3 (GSK3) inhibitor, SB-216763, promotes pluripotency in mouse embryonic stem cells. A. J. Cooney, ed. *PloS One*, 7(6), p.e39329.

Mleczek, M. et al., 2017. Cultivation of mushrooms for production of food biofortified with lithium. *European Food Research and Technology*, 243(6), pp. 1097-1104.

Passmore, L. A. et al., 2007. The Eukaryotic Translation Initiation Factors eIF1 and eIF1A Induce an Open Conformation of the 40S Ribosome. *Molecular Cell,* 26(1), pp. 41-50.

Takahashi-yanaga, F., 2013. Activator or inhibitor ? GSK-3 as a new drug target. *Biochemical Pharmacology,* 86(2), pp. 191-199.

Westermarck, J., 2010. Regulation of transcription factor function by targeted protein degradation: an overview focusing on p 53, c-Myc, and c-Jun. *Methods in molecular biology* (Clifton, N.J.), 647, pp. 31-6.

You, T., Coghill, G. M. & Brown, A. J. P., 2010. A quantitative model for mRNA translation in *Saccharomyces cerevisiae. Yeast,* 27(10), pp. 785-800.

What is claimed is:

1. A method for regulating fungal fruiting body development in a basidiomycetous fungus, comprising:
   (1) administering to the fungus an inhibitor of glycogen synthase kinase-3 (GSK-3); or
   (2) administering to the fungus an siRNA, a dsRNA, a microRNA, a miniRNA, a lncRNA, or an antisense oligonucleotide targeting GSK-3 genomic sequence in the fungus, thereby inhibiting GSK-3 activity in the fungus and delaying or preventing fugal fruiting body development in the fungus when compared with a control fungus not having its GSK-3 activity inhibited.

2. The method of claim 1, wherein GSK-3 activity is abolished.

3. The method of claim 1, wherein GSK-3 activity is inhibited by administration of an siRNA to the fungus.

4. The method of claim 1, wherein GSK-3 activity is inhibited by administration of a dsRNA to the fungus.

5. The method of claim 1, wherein the fungus is an Agaricales fungus.

6. The method of claim 5, wherein the fungus is *Coprinopsis cinerea* or *Pleurotus djamor.*

7. The method of claim 1, wherein the fungus has been administered a GSK-3 inhibitor.

8. The method of claim 7, wherein the inhibitor is administered by injection into the fungus or into a substrate exposed to the fungus.

9. The method of claim 7, wherein the inhibitor is a Lithium (Li)-containing compound or CHIR-99021 HCl.

10. The method of claim 9, wherein the Li-containing compound is Lithium chloride (LiCl).

* * * * *